United States Patent [19]

Zablotowicz et al.

[11] Patent Number: 4,863,866
[45] Date of Patent: Sep. 5, 1989

[54] BRADYRHIZOBIUM JAPONICUM MUTANTS EXHIBITING SUPERIOR SOYBEAN NODULATION

[75] Inventors: Robert M. Zablotowicz, Toronto, Canada; Robert G. Upchurch, Cary, N.C.; James M. Ligon, Peoria, Ill.

[73] Assignee: Lipha Chemicals, Inc., New York, N.Y.

[21] Appl. No.: 24,931

[22] Filed: Mar. 12, 1987

[51] Int. Cl.$^4$ .................. C12R 1/41; C12N 15/00; C05F 11/08
[52] U.S. Cl. .................. 435/252.2; 435/252.3; 435/172.1; 435/878; 71/7
[58] Field of Search .................. 435/172.1, 172.3, 253, 435/878, 252.2, 252.3; 71/7

[56] References Cited

U.S. PATENT DOCUMENTS 4,720,461  1/1988  Urban .................................. 435/253

OTHER PUBLICATIONS

Cho et al. 1985, Kor. J. Appl. Microbiol. Bioeng. 13(1): 79–85.
Kuykendall et al., 1978, Appl. Env. Microbiol. 36(6): 915–919.

*Primary Examiner*—Charles F. Warren
*Assistant Examiner*—David T. Fox
*Attorney, Agent, or Firm*—Foley & Lardner

[57] ABSTRACT

Mutant strains of *Bradyrhizobium japonicum* having enhanced nodulation properties were created by transposon mutagenesis of known *Bradyrhizobium japonicum* strain I-110. The mutant strains grow well in a yeast-extract mannitol medium, produce extracellular polysaccharides at a level greater than the parent strain under appropriate conditions, are capable of growth on a nutirent medium containing a normally inhibitory amount of succinic acid, and contain a 21 Kdalton protein absent from the parent strain. Such strains can be used to inoculate soil in which soybean plants are grown, resulting in improved plant yields.

3 Claims, No Drawings

BRADYRHIZOBIUM JAPONICUM MUTANTS EXHIBITING SUPERIOR SOYBEAN NODULATION

FIELD OF THE INVENTION

This invention relates to *Bradyrhizobium japonicum* mutants exhibiting unusually superior nodulation properties for soybean plants.

BACKGROUND OF THE INVENTION

Prior to the early part of this century natural deposits of nitrate accounted for the major source of nitrogen fertilizer for agriculture. Warnings that these deposits were being depleted and the incentives of approaching war led scientists in 1914 to develop industrial means to fix atmospheric nitrogen. Industrial nitrogen fixation has greatly stimulated agriculture and, in the U.S. alone, the total use of nitrogen fertilizer has increased more than sevenfold since 1948. Industrial production of nitrogenous fertilizer, however, requires large inputs of fossil fuel. Today, the realization of the finite nature of fossil fuel supplies, the worsening world food situation, and a renewed in resource conservation provide incentives to find alternative sources of nitrogen for plant production. It has been estimated that legume-rhizobia symbioses fix biologically as much nitrogen per year as is produced industrially. Biological nitrogen fixation is now being looked upon as a promising nitrogen source for the future. Work on leguminous crops is taking the lead in this effort.

The Gram-negative, aerobic, soil bacteria of the root nodule group comprise two taxonomically distinct genera: the fast growing Rhizobium species and the slow growing Bradyrhizobium species. Al species of rhizobia have the ability to infect leguminous plants and establish a nitrogen fixing symbiosis. The formation of a legume nodule is a complex process involving an array of host and bacterial factors. The interaction of rhizobia and the respective host exhibits specificity. This led early on to the identification of cross-inoculation groups (e.g. C *B. japonicum*-soybean, R. melitoti-alfalfa *R. phaseoli*-bean, *R. leguminosarum*-pea and *R. trifolii*-clover.

Within each Bradyrhizobium species, of which *Bradyrhizobium japonicum* is one, exists a variety of naturally occuring strains which vary in their ability to fix nitrogen in soybeans. Substantial effort has been directed in recent years towards identifying strains having superior nitrogen-fixing characteristics. Such characteristics include the ability of the strain to nodulate the soybean plant and the competitiveness of the strain. Nodulation ability is typically measured by the number of nodules formed on the roots of the mature plant after the roots of the plant, generally as a seedling, are infected with the strain. Competitiveness refers to the ability of the strain to infect (enter) the soybean root to the exclusion of other bacterial strains which occur naturally in the soil.

Testing of naturally occurring *Bradyrhizobium japonicum* strains has led to the identification of the strains best suited for commercial use. Such strains are typically mixed with a particulate carrier, such as peat, and introduced into the soil as a form of fertilizer when the soybeans are planted. The *Bradyrhizobium japonicum* strain thereby has an opportunity to infect the roots of the developing seedling, and the number of nodules formed on the roots of such plants increases over the level it would have been in the absence of the fertilizer containing the strain.

At present the best performing strains of *Bradyrhizobium japonicum* have been identified, and it is unlikely that any significantly better strain, i.e. having better competitiveness and nodulation properties, will be found by screening of naturally occurring strains. Accordingly, research in this area has shifted towards creating artificial, genetically engineered strains of *Bradyrhizobium japonicum* having characteristics superior to any naturally occurring strain. The present invention provides such genetically engineered strains, which strains were created by a genetic engineering technique known as transposon mutagenesis.

The transposon technique has found wide application for introducing random mutations into the genetic material of bacteria. Essentially, the method involves introducing a plasmid, i.e. a circular strand of DNA found in bacteria, from a donor bacterial strain into a recipient bacterial strain. The version of this method used to create the mutants according to the present invention utilizes a so-called "suicide" plasmid, so named because it has no replication ability when removed from cells of its donor bacterial strain and introduced into the cells of the recipient bacterial strain. The suicide plasmid inserts a segment of DNA called a transposon into the large genome present in typical bacterial cells at a more or less random position and interrupts sequences of DNA where introduced. One well-known insertion element is referred to in the art as transposon 5 (Tn5). Tn5 was derived from *E. coli* donor strain 1830 and is readily available from recognized depositories.

Successful insertion of the transposon is indicated by markers, i.e. readily testable characteristics which the genetic material in the transposon imparts to the recipient bacterium. Commonly used marker characteristics are kanamycin resistance, streptomycin resistance and chloramphenicol resistance. The rhizobium strains employed as recipients in the examples below are sensitive to kanamycin and streptomycin but resistant to chloramphenicol, these characteristics being abbreviated $Km^s$, $Str^s$, and $Cm^r$, respectively. For this purpose a suicide plasmid having opposite marker characteristics (i.e. $Km^r$, $Str^r$, $Cm^s$) is employed so that changes in characteristics can be noted. The Tn5 suicide plasmid has been previously employed with Rhizobium japonicum bacteria.

Transfer of the suicide plasmids from donor strain to recipient strain is achieved by the well-known process of conjugation, wherein the donor and recipient bacteria spontaneously form a small tube therebetween which allows exchange of genetic matter. Thus, the transposon mutation technique can be carried out simply by cultivating the donor and recipient strains together under favorable growth conditions. Small samples of the resulting mixture are then treated with the marker substances (e.g. kanamycin) in order to obtain mutant strains wherein insertion of the transposon from the suicide plasmid has occurred.

SUMMARY OF THE INVENTION

This invention provides novel mutant strains of *Bradyrhizobium japonicum*, particularly a mutant hereafter described as mutant strain 119, having superior nodulation characteristics for soybean plants (Glycine max). These strains are genetically engineered mutants created by transposon mutagenesis. The genetic matter of these strains is substantially different from that of the parent strain, U.S.D.A. I-110. In particular, such strains are characterized by some or all of the following characteristics over the parent strain I-110: proliferation on a yeast extract mannitol medium, elevated slime production on a rhizobium defined medium, growth in the presence of succinic acid, which generally inhibits growth of *Bradyrhizobium japonicum* bacteria, the presence of a 21 Kdalton protein absent from the parent strain I-110, and enhanced competitiveness and nodulation properties for soybean plants. Strains having these characteristics may further be employed in a method of cultivating soybean plants which generally includes the steps of fertilizing soil with an inoculum comprising one of the foregoing mutant strains together with a particulate carrier such as peat, then cultivating soybean plants in such soil under conditions allowing the Bradyrhizobium bacteria from the inoculum to infect the roots of the soybean plants.

The present invention further provides a modified mutant *Bradyrhizobium japonicum* genome having genetic means for enhanced nodulation and competitiveness. The chemical structure of this genome is unknown, but it can be definitely characterized by the foreoing properties of the mutant *Bradyrhizobium japonicum* strains.

DETAILED DESCRIPTION OF PREFERRED EXEMPLARY EMBODIMENTS

The mutant strains according to the examples of the invention below are transposon 5 (Tn5) directed mutants of a common *Bradyrhizobium japonicum* strain from the United States Department of Agriculture (USDA) known as strain I-110. After mutagenesis with Tn5, certain mutant clones were selected out of 2000 tested clones because of their superior nodulation and nitrogen fixation capabilities over the parent I-110 strain.

Symbiotic mutants according to the invention of USDA *Bradyrhizobium japonicum* strain I-110 were generated by introduction of Tn5 via conjugation (*E. coli* 1830) of the transposon suicide vector PJB4JI. Kanamycin resistant clones were identified as Tn5 mutants by the criteria of altered phenotype (the mutant is Kanamycin resistant whereas the parent strain I-110 was Kanamycin sensitive) and demonstration of the Tn5 insert by colony hybridization with Tn5 DNA. Two thousand clones were screened on Glycine max (soybean variety Evans) for altered nodulation (nod) and nitrogen fixation (fix) phenotype. All symbiotic mutants thus identified were further characterized for free-living nitrogenase activity. Symbiotic (nod, fix) mutants occurred at a frequency of 1.2%, or roughly 1 mutant in 83.

Ten clones were identified with elevated nodulation (40–60 nodules/plant vs. 18 nodules/plant for I-110). These clones were evaluated for nodulation competency in two soils in greenhouse studies. From these mutants, eight clones were identified that were clearly superior to the parental strain I-110 and, through numerous experiments described in the attached examples, one clone (strain 119) has proven itself to be the single most superior strain. This 119 has been deposited with the Fermentation Laboratory, Northern Regional Research Center, 1815 North University Street, Peoria, Ill. 61604 under the strain names I-110-T-119-1 and I-110-T-119-2, which have been assigned respective deposit Nos. NRRL-B-15822 and NRRL- B-15823.

Strain 119 exhibits up to 2.8 fold higher nodule number compared to its parent when inoculated on soybeans in the absence of other *B. japonicum* bacteria. In addition to increased nodulation, strain 119 exhibits elevated competitiveness, as measured by nodule occupancy over its parent strain (26–80% nodule occupancy compared to 6–17% by the parental I-110) when soybeans inoculated with the described strains are grown in soil containing a native *B. japonicum* population. In addition to the elevated nodulation observed, strain 119 exhibited 5-fold greater nitrogen fixation activity in vitro and 100% greater in planta compared to parental I-110. Strain 119 no longer harbors the Tn5 transposon, but has maintained the elevated symbiotic characteristics. In field studies in soils containing a high population of native *B. japonicum*, strain 119 exhibited 6–36% nodule occupancy compared to 0–6% occupancy by the parental strain. Consistent yield enhancement has been observed at some locations as a result of soybean inoculation with this mutant. The foregoing results are described in detail below.

Hybridization studies of strain 119 DNA demonstrated that the Tn5 transposon DNA was apparently lost from strain 119 and other mutants. The loss of the transposon did not affect the superior characteristics of strain 119.

Strain 119 is thus a novel clone that does not exist in nature and is distinguishable from its parental strain I-110 based on:

1. Nodule occupancy under defined laboratory conditions
2. Nodule occupancy under greenhouse conditions
3. Nodule occupancy and yield in one year of field trials
4. Rapidity of nodulation on soybean roots
5. Expression of unique proteins by strain 119
6. Expression of biochemical characteristics that are different from the parent I-110 (See Table 14 below).

Parental strain I-110 is representative of the best *B. japonicum* strains presently available.

Transposon mutagenesis is a powerful, well-known method for genetic analysis in bacteria and is therefore particularly appealing for the study of symbiotic properties of Rhizobium. While a fairly extensive body of literature has accrued over the past few years from transposon genetic studies of the fast-growing rhizobia, much less information is available for the slow-growing rhizobia such as the soybean microsymbiont *Bradyrhizobium japonicum*. According to the present invention, the suicide plasmid method of Beringer has been adopted to isolate kanamycin resistant mutants of *B. japonicum* USDA strain I-110 that are enhanced in the symbiotic properties of nodulation and nitrogen fixation as will be described hereafter. (See Beringer, J. E., J. L. Beynon, A. V. Buchanan-Wollaston, and A. W. B. Johnston (1978), "Transfer of the Drug-Resistance Transposon Tn5 to Rhizobium," *Nature*, 276:633–634; and Kuykendall and Elkan, "Rhizobium japonicum Derivatives Differing in Nitrogen-Fixing Efficiency and Carbohydrate Utilization," *Applied Environ. Microbiol.* 36:915–919.

EXAMPLE 1.

Mutagenesis of Parental Strain I-110 and Selection of Superior Mutant Clone strains.

Transposon Tn5 Mutagenesis

Introduction of the Tn5 donor "suicide" plasmid PJB4JI to USDA *Bradyrhizobium japonicum*. I-110 was by conjugation from the E. coli donor strain 1830 (Km$^r$, Str$^r$, Cm$^s$) to the rhizobial recipients (Km$^s$, Str$^s$, Cm$^r$) using the filter mating technique described by Cen et al. (Cen, Y., G. L. Bender, M. G. Trinich, N. A. Morrison, K. F. Scott, P. M. Gresshoff, J. Shine, and B. G. Rolfe, 1982, "Transposon Mutagenesis In Rhizobia Which Can Nodulate Both Legumes and the Nonlegume Parasponia," Applied and Environ. Microbiol. 43:233–236.) Two ml. each of the recipient culture in mid-log phase and an overnight culture of the donor strain were mixed and filtered onto a 0.45 micron filter. The filter was placed on agar for 24 hours at 28° C. after which the cells were resuspended in 5 mls. of broth and plated in 100 microliters aliquots on agar plates containing 500 micrograms kanamycin/ml. and 50 micrograms chloramphenicol/ml. After 7–10 days Km$^r$ Bradyrhizobium colonies were selected. The frequency of Km$^r$ colonies after conjugation is shown in Table 1.

TABLE 1

TRANSFER OF THE TRANSPOSON
TN5 DONOR PLASMID PJB4JI
AND TN5 MUTAGENESIS AND
THE COSMID VECTOR PLAFR1

|  | Frequency of Antibiotic Resistance | | |
| --- | --- | --- | --- |
|  | B. japonicum | Cowpea Rhizobia | |
|  | USDA I-110 | 32H1 | CB756 |
| Spontaneous Km$^r$ | $10^{-8}$ | $10^{-8}$ | $10^{-8}$ |
| Spontaneous Tc$^r$ | $10^{-9}$ | ND[1] | ND |
| Transfer of PJB4JI and Tn5 Transposition (Km$^r$) | $7 \times 10^{-7}$ | $6 \times 10^{-7}$ | $9 \times 10^{-7}$ |
| Transfer of PlAFR1 (Tc$^r$) | $7 \times 10^{-5}$ | ND | ND |

[1]Not determined

Spontaneous Km$^r$ and Tc$^r$ refer to the frequency at which these characteristics occur naturally in a given population of the indicated strain. In B. japonicum, the Tn5 transposition increased the frequency of kanamycin resistance (Km$^r$) by a factor of 70. The antibiotic resistance frequency for PlAFR1 transfer is also included for purposes of comparison. The increase in antibiotic resistance noted for the Tn5 transposition was intermediate the spontaneous level for such antibiotic resistance but not nearly as great as the change caused by PlAFR1 transfer for Tc$^r$.

Plant Screening for Symbiotic Mutant Phenotypes:

2000 Km$^r$ mutants resulting from recombination of I-110 DNA with Tn5 DNA (abbreviated I-110::Tn5) were screened on soybean plants (Glycine max, Evans cultivar) to identify those mutants altered in symbiotic capabilities. Each mutant was used to inoculate four soybean seedlings. After 35 days of growth the symbiotic performance of each mutant was compared to that of the I-110 parent and uninoculated controls. The parameters used to determine symbiotic competence were (1) plant color, (2) whole plant acetylene reduction activity, a reliable indicator of nitrogen fixing ability, and (3) total number of nodules/plant. Approximately 1.2% of the mutants screened were identified as having altered symbiotic phenotypes, i.e. having substantially different properties from the parent strain. The mutants identified in the first plant screening were tested a second time on soybean plants with five replicates. The altered phenotypes determined in the second screening generally were identical to the results of the first screen. Mutant clone strain 119 was one of eight clones to demonstrate altered characteristics superior to the parent I-110, as indicated in the following Table 2:

TABLE 2

SYMBIOTIC PROPERTIES OF USDA
BRADYRHIZOBIUM JAPONICUM
STRAIN I-110 AND
MUTANT CLONE STRAIN 119

| Strain Designation | Nodule Number | ARA/ Plant | ARA/Free- Living | Plant Color |
| --- | --- | --- | --- | --- |
| I-110 | 19.6 ± 4.4 | 2.6 ± 0.5 | 42.6 ± 3.4 | 4.0 |
| strain 119 | 41.3 ± 3.2 | 3.6 ± 0.2 | 61.4 ± 2.7 | 4.0 |

In the preceding Table 2, "Nodule Number" refers to the average number of nodules per plant. ARA refers to acetylene reduction activity, for which two replications were performed, the amounts indicated being in nMoles $C_2H_2$ per hour per milligram of protein. Plant color was rated at 35 days on a scale from one to four, one being yellow and stunted, four being dark green and healthy. ARA/Plant refers to the acetylene reduction activity of the strain when in the plant, whereas ARA/Free-Living refers to the acetylene reduction activity in a free-living state outside of the soybean plant. As the table shows, strain 119 is greatly superior to its parent strain in nodulation, acetylene reduction activity, and equal thereto as regards plant color.

EXAMPLE 2

Free-Living Nitrogenase Activity Screens of Symbiotic Mutant

Free-living nitrogenase activity of the I-110 parent and mutant strains was determined by the soft agar overlay method of Pankhurst and Craig. (Pankhurst, C. E. and A. S. Craig., 1978, "Effect of Oxygen Concentration, Temperature and Combined Nitrogen on the Morphology and Nitrogenase Activity of Rhizobium Sp. Strain 32H1 in Agar Culture," G. Gen. Microbiol. 106:207–219.) After the acetylene reduction assay was completed, the rhizobial cell-impregnated soft agar disc was floated out of the assay vial, digested with 0.3N NaOH at 90° C., and whole cell protein determined by the method of Lowry et al. (Lowry, O. H., N. J. Rosenbrough, A. L. Farr, and R. G. Randall., 1951, "Protein Measurement with the Folin Phenol Reagent," J. Biol. Chem. 193:265–275.)

EXAMPLE 3

Symbiotic Evaluation of Mutants and Selection of Clone strain 119 with In-Planta Tests Rhizobial cultures for inoculation were grown on yeast extract broth to an optical density of approximately 1.0 (640 nm). Sterile urine jars filled with sterile vermiculite were used for plant growth. Soybean seeds (Glycine max L. merr. ) 'Evans' cultivar, were surface sterilized in 70% ethanol for 2 min., rinsed thrice in sterile distilled water and pregerminated in sterile vermiculite for 48 hours at 28° C. Seedlings were transplanted aseptically into the sterile urine jar assemblies, inoculated with 1.0 ml of culture and covered with vermiculite. Plants were maintained for 28 days in a growth chamber at a 14 hour photoperiod with a maximum light intensity of 300 μEinsteins cm$^{-1}$ sec$^{-1}$ with a maximum/minimum temperature of 28°/23° C. Typically 100–150 mutants were evaluated in one experiment arranged in four replicate blocks as a randomized block design. Eight uninoculated controls and eight I-110 parents were included in each planting. Plants were irrigated as needed with filter sterilized deionized water with no additional nutrient solution added.

Following the 32–35 days of growth, plants were harvested for acetylene reduction assays and nodule evaluation. For acetylene reduction assays, single roots were placed in 250 ml. Erlenmeyer flasks, stoppered with a rubber stopper containing a glass tube fitted with a rubber septum. Acetylene was added to approximately 10% volume and the roots were incubated for one hour at ambient temperature prior to gas sampling. Ethylene concentration in the incubation chamber was determined on a Perkin Elmer Sigma 2b gas chromatograph fitted with a one m Poropak N column and a flame ionization detector. Nitrogen was utilized as the carrier gas at a flow rate of 30 ml/min., 50° C. oven temperature and a 150° C. detector temperature. Following acetylene reduction, assays of nodule number per plant were scored. Mutants exhibiting nodulation or fixation phenotypes altered from the parental strain were retested in a second in planta test utilizing the above protocol.

Of two thousand Tn5 mutants of I-110 evaluated in the first screen, eight mutants (Table 3) were identified that exhibited significantly greater nodulation than the parental type. A repeated evaluation confirmed that at least five of the eight mutants (119, 151, 152, 298 and 327) were significantly elevated in comparison to the parental type. Many had a nodule number of 40 or more, twice the nodule number of the parent strain (see Table 3 below). Nitrogenase activity based upon the acetylene reduction assay indicated that two of the eight elevated nodulation mutants (strains 119 and 152) also exhibited superior symbiotic fixation rates greater than 3.0 micromoles/plant/hour (see Table 4 below). All elevated nodulation mutants were derived by transformation with PJB4JI.

TABLE 3

NODULATION OF 28 DAY OLD 'EVANS' SOYBEANS AS INFLUENCED BY INOCULATION OF B. JAPONICUM I-110 AND ENHANCED NODULATION MUTANTS IN TWO STUDIES (I & II)

| Strain | No. of nodules per plant: Study I | Study II |
|---|---|---|
| I-110 parental | 18 | 16 |
| 119 | 45 | 45 |
| 151 | 55 | 54 |
| 152 | 48 | 36 |
| 158 | 46 | 24 |
| 165 | 55 | 25 |
| 193 | 60 | 16 |
| 298 | 39 | 41 |
| 327 | 40 | 70 |

TABLE 4

NODULE NUMBER AND ACETYLENE REDUCTION ACTIVITY OF PARENTAL STRAIN I-110 AND EIGHT CLONES ON 'EVANS' SOYBEANS

No. of Nodules Per Plant at end of Four Weeks

| Strain | Avg. Nodule No./Plant (Average 2 repetitions, 4 plants per repetition) |
|---|---|
| I-110 parental | 23 |
| 119 | 45 |
| 151 | 52 |
| 152 | 42 |
| 158 | 35 |
| 165 | 40 |
| 193 | 38 |
| 298 | 40 |
| 327 | 65 |

| Strain | Acetylene Reduction Activity Avg. micromole/plant/hour (Average 2 repetitions, 4 plants per repetition) |
|---|---|
| I-110 parental | 1.7 |
| 119 | 3.6 |
| 151 | 1.9 |
| 152 | 3.2 |
| 158 | 2.5 |
| 165 | 1.6 |
| 193 | 1.8 |
| 298 | 2.5 |
| 327 | 2.2 |

EXAMPLE 4

Nodule Occupancy of Clone strain 119 Compared to Parental Strain I-110 Under Laboratory Controlled Conditions Growth room studies were conducted to further confirm the superior competitiveness of strain 119 for nodule forming sites when challenged against the parental strain I-110 on the soybean cultivar "Centennial" under bacteriologically controlled conditions. In the first study, I-110 was utilized as a control. In the second study, strain 119 was challenged with an antibiotic resistant strain of parental I-110 to confirm results and also monitor double infections. This mutant is both streptomycin and rifampicin resistant.

Seeds were surface sterilized by immersion in 95% ethyl alcohol for two minutes and rinsed with sterile distilled water followed by immersion in 1% calcium hypochlorite for two minutes. Then the seeds were exhaustively rinsed with sterile distilled water and soaked for one hour in the final rinse. Disinfected seeds were germinated overnight in a sterile vermiculite bed at 28° C. to yield seedlings with radicals of 0.5 to 2.0 cm in length.

Sterile, pregerminated seedlings were aseptically transferred to modified Leonard jar assemblies containing sterile sand, vermiculite (1:1 v/v) potting mix which was moistened with one-half strength plant nutrient solution according to the method of Evans et al. modified by adding 1 mM $KNO^3$. Subsequent waterings were done with distilled deionized $H_2O$. Seedlings were inoculated with 0.5 ml. of single strain or mixed inoculant as prescribed ($1 \times 10^8$, cells $ml^{-1}$) at ratios indicated on Table 6. Eight replicates were utilized in the I-110 parent study and six replicates were used in the strain 119/I-110 study. The experiment was arranged in a randomized complete block design and the plants were grown for 35 days under the following regime: daylength, 14 hours; lighting, variable, 300 μEinsteins $cm^{-1}$ $second^{-1}$ maximum intensity; temperature, 27°±1° C. day, 23° C. night; relative humidity, 65%. For nodule assessment plants were harvested, roots washed, and nodules typed by antibiotic resistance recovery utilizing the nodule typing technique as follows.

Two 96 well, U-bottom, 250 microtiter test plates were used to form the sterilization chamber. The lower plate had sixteen 1 mm holes drilled in alternate patterns in rows A, C, E, G and columns 3, 5, 7, and 9 to facilitate movement of sterilants and rinsing water into the chamber. The top plate or cover was a standard microtiter plate which, after the lip and 3 mm are milled off the plate bottom, fitted precisely into the lower plate. Once nodules were placed in each of the 16 wells, the cover was put in place and the chamber held together with two large binder clips.

A nodule replicator simultaneously served as a crusher and multi-inoculator. It was constructed from a microtiter plate from which the lip had been milled and 16 steel finishing nails (#16, 3/4 in.) had been affixed with epoxy cement in a pattern corresponding to that of the location of the nodules in the sterilization chamber. The nailheads extend 11 mm beyond the bottom of the wells, enough to reach the bottom of the receiving well containing the nodule. Wire handles were attached to the template through holes drilled in the corners of the plate to facilitate handling and plating. The replicator was sterilized by immersion in 70% ethyl alcohol for 1–2 minutes and then allowed to air-dry in a laminar flow hood.

Roots were washed in dilute detergent solution to remove adhering potting material. Sixteen nodules were usually selected from each plant, with equal emphasis given to top and lateral nodules. After the sterilization chambers were loaded with 16 nodules each, they were sterilized via sequential immersion in 1:4 (v/v) dilution of commercial bleach (5.25% sodium hypochlorite) for 1–2 minutes, 70% ethyl alcohol for 1–2 minutes, and 3 rinses of 0.5–1 minute in sterile distilled water. Sterile water and disinfectant baths were exchanged every 30 or so templates processed. Time of disinfection was adjusted according to nodule size: smaller nodules (2–3 mm) for one minute in each disinfectant solution and 2 minutes for nodules greater than 4 mm. All operations were conducted on the bench top except the final rinse which was conducted in a laminar flow hood.

Platings were carried out on standard yeast extract mannitol agar. Each petri plate (15 × 100 mm) contains 32 ml. of agar to facilitate the inoculation procedure. Antibiotics were used in the following concentrations: kanamycin sulate, 500 micrograms/ml; rifampicin, 150 micrograms/ml; streptomycin sulfate, 500 micrograms/ml; cycloheximide, 200 micrograms/ml; and trimethoprim, 10 micrograms/ml. The last two antibiotics were included in all media to control fungal and enteric bacterial contaminants, respectively. Strain 119 was plated on kanamycin, rifampicin media, while I-110 was plated on streptomycin, rifampicin media.

The sterile nailheads were fitted into the corresponding 16 wells containing nodules and a rocking motion was applied to effectively crush the nodules and transfer inoculum onto the nailheads. Nodule juice was transferred to selective agar via the nailheads. Plates were incubated at 28° C. for 11 days in the dark prior to scoring of nodule occupancy.

The relative competitiveness of parental strain I-110 and strain 119 when challenged according to the preceding procedure is indicated in Table 5. In Table 5, the two left columns indicate the makeup of the inoculum used to infect the plants. The inoculum was a mixture in most cases of I-110 parental (not antibiotic resistant) and the antibiotic resistant mutant, either the I-110 parental mutant or strain 119. The two right colums of Table 5 indicate the percentage of the antibiotic resistant mutants in the nodules upon completion of the experiment. In general, if the antibiotic resistant mutant has a greater competitiveness than the I-110 parental strain, then the percentage thereof found in the nodules will be greater than the percentage of the antibiotic resistant mutant in the initial inoculum. If there is no difference in competitiveness, then the percentages should be roughly equal. An antibiotic resistant mutant of the I-110 parental strain was employed to illustrate that the genetic factors for antibiotic resistance are not critical to increased competitiveness, i.e. the I-110 antibiotic resistant mutant did not have substantially greater competitiveness than the I-110 parental strain lacking antibiotic resistance.

A fairly linear relationship exists between nodule occupancy of I-110 and percent I-110 in the inoculum, indicating that I-110 and the I-110 (antibiotic resistant mutant) are similar in competitiveness. By contrast, when strain 119 is 10% of the inoculum, it is the occupant of approximately 35% of the nodules. At the 10% and 50% concentrations, strain 119 occupies significantly more nodules than does I-110, again demonstrating the superior competitiveness of strain 119.

These observations are likewise verified in the I-110/strain 119 challenge (Table 6) wherein strain 119 was again proved an efficient competitor, especially at the 10% and 50% strain 119 dilutions. In Table 6, the three nodule occupancy percentages for strain 119, strain I-110 parental, and for mixed strains add up to 100%. Nodules containing both strain 119 and I-110 parental were characterized as mixed strains.

TABLE 5

NODULE OCCUPANCY OF CENTENNIAL SOYBEANS BY B. JAPONOCUM MUTANTS I-110 AND STRAIN 119 AS INFLUENCED BY VARYING PROPORTIONS OF WILD TYPE STRAIN I-110 AND THE ANTIBIOTIC RESISTANT MUTANTS IN THE INOCULUM

| Initial I-110 Parental in inoculum (%) | Initial antibiotic resistant mutant in inoculum | Nodule Occupancy - antibiotic resistant mutants | |
|---|---|---|---|
| | | I-110 Parental (%) | 119 (%) |
| 100 | 0 | 0 | 0 |
| 99 | 1 | ND[a] | 6.3 ± 1.2[b] |
| 90 | 10 | 12.5 ± 2.0 | 34.6 ± 2.3[c] |
| 50 | 50 | 52.6 ± 3.0 | 67.2 ± 3.1[c] |
| 10 | 90 | 88.9 ± 2.5 | 92.9 ± 2.2 |
| 1 | 99 | 94.5 ± 1.4 | 95.2 ± 2.3 |
| 0 | 100 | 100 | 100 |

[a]Not determined.
[b]Mean and standard error of the mean of eight replicates.
[c]Mean occupancy of strain 119 is significantly greater (p = .05) than occupancy of parental strain I-110.

TABLE 6

NODULE OCCUPANCY OF CENTENNIAL SOYBEANS AS INFLUENCED BY VARYING PROPORTIONS OF STRAIN 119 AND I-110 IN THE INOCULUM

| Strain ratio Strain 119/I-110 | Nodule Occupancy (%) | | |
|---|---|---|---|
| | Strain 119 | I-110 Antibiotic resistant strain | Mixed (both strains present |
| 0:100 | 0 | 100 | 0 |
| 1:99 | 1.1 ± 1.0[a] | 95.6 ± 2.8 | 3.3 ± 2.8 |
| 10:90 | 30.5 ± 13.2 | 50.3 ± 12.3 | 20.2 ± 4.9 |
| 50:50 | 47.6 ± 9.0 | 25.8 ± 6.5 | 26.6 ± 9.1 |
| 90:10 | 83.3 ± 8.6 | 12.8 ± 6.4 | 3.9 ± 2.5 |
| 99:1 | 100 | 0 | 0 |
| 100:0 | 100 | 0 | 0 |

[a]Mean and standard error of the mean of six replicates.

EXAMPLE 5

Nodule Occupancy and Selection of Clone Strain 119 Compared to Parental Strain I-110 on In Planta Evaluations in Natural Soils (Greenhouse Studies)

The eight Tn5 mutants originally identified as elevated nodulation mutants were evaluated for competitiveness in native soils containing a population of indigenous rhizobia, the hypothesis being that a rhizobial mutant exhibiting enhanced nodulation might have a competitive advantage over naturally occurring strains.

Two soils were utilized for this study, a Cecil sandy loam from Athens, Ga. and a Crowley silt loam from Crowley, La. These soils contained approximately $10^5$ B. japonicum per one gram soil. Surface disinfected plastic pots 100 mm diameter, 100 mm deep were filled with a 50/50 v/v mixture of the soil and sterile sand. Four surface sterilized pregerminated (48 h) Centennial or Wright soybean seeds were planted per pot and 0.5 ml of yeast extract broth culture of the mutants or the parental I-110 were inoculated onto each seed. The experiment was designed as a randomized complete block with five replications and appropriate controls. Following 35 days of growth, plants were harvested and nodules were typed utilizing immunodiffusion serological techniques with antiserum prepared specifically against B. japonicum strain 3Ib110. Twelve nodules per plant or 24 per pot were typed with this technique.

Cultivar (plant type) and soil type both had a substantial effect on nodule occupancy by strains of serogroup 110, as shown in Table 7. Significantly greater occupancy by serogroup 110 was identified in plants inoculated with strain 119. Although five mutants exhibited an elevated nodulation phenotype, only one mutant, strain 119, exhibited enhanced competency over the natural rhizobial populations already present in the soil samples tested. In Table 6, the nodule occupancy of the natural rhizobia is 100% minus the indicated value for I-110 and the mutant strains.

TABLE 7

NODULE OCCUPANCY BY SEROLOGY AS INFLUENCED BY INOCULATION WITH TN5 MUTANTS ON SOYBEAN WRIGHT (W) AND CENTENNIAL (C) CULTIVARS

| | % Nodule Occupancy | | | |
|---|---|---|---|---|
| | Georgia Soil | | Louisiana Soil | |
| Strain | W | C | W | C |
| I-110 parental | 6 | 17 | 14 | 18 |
| strain 119 | 26 | 61 | 77 | 81 |
| 151 | 0 | 3 | 17 | 10 |
| 152 | 3 | 5 | 13 | 28 |
| 158 | 4 | 9 | 17 | ND |
| 165 | 0 | 0 | 8 | 31 |
| 193 | 0 | 0 | 12 | ND |
| 298 | 13 | 9 | 25 | 31 |
| 327 | 0 | 5 | 10 | 7 |
| Uninoculated | 0 | 0 | 0 | 0 |

ND = Not determined due to insufficient amounts of antisera for detection.

EXAMPLE 6

Comparison of Nodule Occupancy and Soybean Yields Between Clone Strain 119 and Parental Strain I-110 Field Trials In one growing season, strain 119 was compared with the parental strain I-110 in five southern U.S. field sites containing an indigenous population of B. japonicum. The soybean cultivar 'Centennial' was utilized in the Arkansas, Louisiana, and South Carolina trials and the 'Braxton' cultivar in the Alabama and Georgia trials. Soybeans were inoculated by application of approximately 0.6 gram per meter of row of granular peat inoculum (approximately $5 \times 10^{-8}$ cells per gram of peat). Treatments were replicated five times with plots of 8 meters long with row spacing of approximately 0.75 m with six rows per plot.

Soybeans were sampled for nodule occupancy 35 and 56 days after planting. Roots were excavated, washed and shipped on ice. Nodules were typed serologically as described in Example 5 with 60 nodules per treatment for each of five replicate plots. Yields were obtained by row harvest of all plots at plant maturity.

Tables 8 and 9 summarize the results. At both harvests, the parental strain I-110 exhibited poor establishment in the nodules as evident by a low (approximately 2%) overall nodule occupancy (Table 8). The mutant strain 119, by contrast, was more aggressive with an overall occupancy of 18.1% at 35 days after planting and 9.9% at 56 days after planting. Thus, strain 119 is more competitive than the parent strain in growth chamber pot studies under bacterio-logically controlled conditions (Example 4), in soil pot studies (Example 5) and under field conditions (Example 6).

Strain 119 was responsible for yield increases superior to strain I-110 at Georgia (GA) and Arkansas (AR) while I-110 was superior in Louisiana (LA). There were no differences in Alabama (AL) and South Carolina (SC) and the averages over all five locations indicate strain 119 more favorable overall, but not beyond the limits of experimental uncertainty. (See Table 9). Strain I-110 was superior to the uninoculated control at two of five sites (AL and LA) while clone strain 119 was superior to the control at three of five sites (AL, GA, and AR). Averaged over all five sites, clone strain 119 resulted in an 11.7% increase in yield over the uninoculated control while strain I-110 provided a 5.1% increase in yield (See Table 10). This indicates that clone strain 119 has a yield enhancement effect as well as superior nodule occupancy.

TABLE 8

INFLUENCE OF B. JAPONICUM INOCULATION ON NODULE OCCUPANCY BY STRAIN I-110 AND CLONE STRAIN 119 AT FIVE SOUTHERN U.S. LOCATIONS AT 35 AND 56 DAYS AFTER PLANTING (DAP)

| | 35 DAP | | 56 DAP | |
|---|---|---|---|---|
| LOCATION | I-110 | 119 | I-110 | 119 |
| Alabama | 1.0 | 6.3 | 0.3 | 4.0 |
| Arkansas | ND | ND | 0.7 | 16.0 |
| Georgia | 0.0 | 2.8 | 0.3 | 3.3 |
| Louisiana | 2.7 | 36.3 | 3.0 | 7.3 |
| South Carolina | 3.3 | 28.0 | 6.0 | 19.0 |
| Mean ± SD[1] | 1.8 ± 0.7 | 18.1 ± 7.1 | 2.1 ± 1.0 | 9.9 ± 2.9 |

[1]SD = One Standard Deviation

TABLE 9

SOYBEAN YIELDS (BUSHEL/ACRE) AT FIVE SITES AS INFLUENCED BY INOCULATION WITH STRAIN I-110 OR CLONE STRAIN 119

| | Southeast States | | | Delta States | | Average |
|---|---|---|---|---|---|---|
| Treatment | AL | GA | SC | AR | LA | & SD[1] |
| I-110 | 41.5a[2] | 21.0a | 42.8a | 47.9a | 37.0b | 38.0 ± 4.1 |
| 119 | 42.2a | 27.0b | 43.4a | 50.3b | 32.6a | 39.1 ± 3.7 |

TABLE 9-continued

SOYBEAN YIELDS (BUSHEL/ACRE) AT FIVE SITES AS INFLUENCED BY INOCULATION WITH STRAIN I-110 OR CLONE STRAIN 119

|  | Southeast States | | | Delta States | | Average |
|---|---|---|---|---|---|---|
| Treatment | AL | GA | SC | AR | LA | & SD[1] |
| Control[3] | 38.1b | 18.0a | 43.4a | 46.1a | 32.1a | 34.9 ± 4.7 |

[1]SD = One Standard Deviation
[2] = Values labelled "b" are significantly different statistically from values labelled "a" in the same column, and represent a greater difference than can be attributed to experimental uncertainty.
[3] = Controls were plots that were not inoculated at planting.

TABLE 10

EFFECT OF INOCULATION ON AVERAGE SOYBEAN YIELDS ACROSS THE FIVE SITES

| Strain | Average Seed, Yield in Bushels Per Acre (Bu/A) | Average Increase Over Control (%) |
|---|---|---|
| 119 | 39.4 | 11.3 |
| I-110 | 38.0 | 9.2 |
| Uninoculated control | 34.9 | — |

Recovery of introduced *B. japonicum* from nodules of soybeans at five and eight weeks of growth in five southern states has been completed. At early stages of plant growth (Table 9), the most competitive strain across all locations was strain 119. In Table 8, recovery of strain 119 averaged 18.1% for the five locations, and this was 110 times the recovery of its parent, I-110. The highest recovery of strain 119 at any one site was about 36%. At the later stages of plant growth recovery of all strains was generally low, as expected. From these recovery data, strain 119 emerges as a strain having superior competitiveness.

EXAMPLE 7

Comparison of Rate of Nodulation on Soybeans Between Parental Strain I-110 and Clone strain 119

A comparison of nodulation over time of strain 119 and I-110 was conducted. Soybean cultivar 'Centennial' seeds were surface sterilized and germinated for 48 hours prior to transplanting in modified Leonard jar assemblies (2/pot). Seedlings were inoculated with 0.5 ml. of culture ($1 \times 10^9$ cells/ml) and maintained in a growth chamber as previously described. The experiment was set up as a randomized complete block of ten replicate blocks of five pots per block per strain. Plants were harvested and nodules counted at 7, 11, 14, 18 and 21 days after planting.

At day 7, clone strain 119 exhibited significantly greater nodulation than the parent I-110. This trend was statistically similar until day 18 (Table 11). The capacity for early nodulation may be one of the reasons why strain 119 is more competitive than I-110.

TABLE 11

NODULATION OF 'CENTENNIAL' SOYBEANS AT FIVE HARVEST DATES AS INFLUENCED BY INOCULUM

| Strain | Nodules/Plant | | | | |
|---|---|---|---|---|---|
|  | Day 7 | Day 11 | Day 14 | Day 18 | Day 21 |
| 119 | 8.4[a] | 33.5[a] | 33.5[a] | 26.0[a] | 26.5[a] |
| I-110 | 1.1[b] | 15.5[b] | 19.5[b] | 21.5[a] | 22.0[a] |

In the preceding table, "b" values are statistically different than "a" values as noted above in connection with Table 9.

EXAMPLE 8

Characterization of Protein Patterns by SDS-PAGE Between Parental Strain I-110 and Clone Strain 119

Polyacrylamide gel electrophoresis in the presence of sodium dodecyl sulfate (SDS-PAGE) is now recognized as the most definitive method for examining polypeptide profiles of subcellular proteins. This method has been suitably adapted and used to characterize soluble proteins of different groups of rhizobia. When SDS-PAGE was used to examine the soluble proteins of the mutant strain 119 and its parent, I-110, substantial quantities of a 21 Kdalton protein were found in strain 119 which were essentially absent from I-110.

Several variables that could influence the production, stability, and detection of the protein were examined. These were: (a) protein expression during growth in a complex yeast extract mannitol medium (YEM) as opposed to growth in a defined medium containing gluconate and yeast extract (RDY); (b) the effect of heating cell-free extracts at 85°–90° C. for three minutes; (c) staining gels with Coomassie Brilliant Blue and or the Bio. Rad silver stain; (d) electrophoresis of dissociated versus nondissociated proteins; and (e) the use of gradient versus single concentration gels. For comparison purposes, three other strains of the 110 serogroup were included: USDA 110, L-110, and GS-110.

The 21 Kdalton protein was better separated in a 9–12% gradient concentration gel than in a single concentration gel of 10.0%, 10.5% or 11.0% polyacrylamide. It was also more strongly stained by the silver than the Coomassie Blue stain. The best procedure for visualizing the protein profiles of any of the strains, however, was achieved when gels were first stained with silver then subjected to the Coomassie Blue stain. The 21 Kdalton protein was detected in the strains whether they were grown in YEM or RDY, whether cell extracts were heated or not, and whether or not cell extracts were treated with SDS and 2-mercaptoethanol to dissociate proteins into polypeptides. None of these treatments enhanced recovery of the protein from extracts of either strain. The 9–12% polyacrylamide gel was stained in silver and then Coomassie Brilliant Blue.

In both heated and unheated preparations, the presence of a large 21 Kdalton protein band in clone strain 119 was apparent. This same band was either absent or present in only trace amounts in parental strain I-110.

EXAMPLE 9

Comparison of Biochemical Characteristics of Parental Strain I-110 and Clone Strain 119

This example compares I-110 and strain 119 in a series of standard tests that are commonly used to characterize strains of *Bradyrhizobium japonicum*.

9A. Growth in YEM and Slime Production on RDY

Parental I-110 and strain 119 were evaluated for growth on yeast-extract-mannitol (YEM) agar and Bradyrhizobium dfined agar (RDY). The compositions of these media are:

| YEM | | RDY | |
|---|---|---|---|
| $K_2HPO_4$ | 0.5 g | $K_2HPO_4$ | 1.0 g |

-continued

| YEM | | RDY | |
|---|---|---|---|
| MgSO$_4$.7H$_2$O | 0.2 g | KH$_2$PO$_4$ | 1.0 g |
| NaCl | 0.1 g | FeCL$_3$.6H$_2$O | 0.01 g |
| Mannitol | 10.0 g | MgSO$_4$.7H$_2$O | 0.25 g |
| Yeast Extract | 0.4 g | CaCl$_2$.6H$_2$O | 0.1 g |
| Distilled Water | 1600 ml | NH$_4$NO$_3$ | 0.08 g |
| | | Mannitol | 10.0 g |
| | | Vitamins* | 100 microliters |
| | | Trace Elements** | 100 microliters |
| | | Distilled Water | 1000 ml |

*Vitamin Mixture - 1.0 g/ml of each of Biotin, Pantothenic acid, and Thiamin.
**Trace Elements - 1.0 g/ml of each of Cobalt, Molybdenum, Zinc, Boron, and Manganese.

After adding agar (15 g/l) and preparing the media, I-110 and strain 119 were suspended separately in dilution bottles (100 cells/ml) and 1.0 ml was spread over agar plates. Incubation was at 25° C. for 14 days. Strain 119 grew rapidly on both media and formed large, gummy colonies within 10 days. I-110 grew more slowly on YEM, but was equal to strain 119 on RDY. However, strain 119 produced double the amount of slime (extracellular materials) on RDY as did I-110. Slime production on YEM was equivalent for both cultures (see Table 14). The comparison of slime production was performed by a standard procedure for staining lipid materials with Sudan Black.

9B. Growth on Succinate Media

I-110 and strain 119 were evaluated for growth on yeast extract mannitol (YEM) agar and Bradyrhizobium defined agar (RDY) containing a growth-inhibiting amount (5.0 g) of succinic acid (neutralized to pH 7.0) in the media. As used herein, a "growth-inhibiting amount" is an amount of succinic acid sufficient to inhibit the growth of most known strains of *Bradyrhizobium japonicum* serogroup 110, 122, 123, IC-1 in a nutrient medium such as RDY to the extent of no growth or only trace growth. Following seven days after inoculation, strain 119 exhibited abundant growth, while the parent strain I-110 was incapable of growth on either media (See Table 14). "Abundant growth" as referred to herein means colonies several times (e.g. at least three times) greater in number and/or density as produced by the parent strain under the same conditions. However, parental I-110 was capable of growth on both media in the absence of the succinate.

Known strains of *Bradyrhizobium japonicum* are generally intolerant of succinate and will not grow on media to which it has been added. Strain 119 is thus distinguishable from most other strains of *B. japonicum* because it thrives in the presence of succinic acid.

9C. Hydrogen uptake (Hydrogenase Activity)

I-110 and the eight superior nodulation mutants were evaluated for free living hydrogen uptake utilizing standard techniques. Cells were grown under a controlled atmosphere (87% N$_2$, 5% CO$_2$, 5% H$_2$ and 1% O$_2$) for seven days in hydrogen uptake media for derepression of hydrogenase. Hydrogen uptake was determined amphoterically utilizing an O$_2$ electrode with reversed polarity. Similar levels of H$_2$ uptake were observed with all mutants and were not different from parental I-110 (see Table 12).

9D. Free living N$_2$ Fixation (Nitrogenase Activity

I-110 and eight mutant clones of the invention were evaluated for free living nitrogen fixation ability utilizing standardized techniques, under derepression conditions in soft agar, in an atmosphere of 89% O$_2$, 10% Acetylene and 1% O$_2$. Ethylene was determined 12 days after inoculation utilizing gas chromatography. Protein content of the inoculum was determined utilizing the Lowry method.

As indicated in Table 13, I-110 exhibited a relatively low rate of ethylene accumulation as did most other clones, the exception being strain 119 which consistently reduced five fold more acetylene than the parental type. Thus in both symbiotic and in free living conditions, strain 119 was superior to the parent I-110.

9E. 110 Somatic Agglutination

Antiserum against I-110 was prepared in rabbits following standard immunological procedures for injection, bleeding, recovery, and purification of antisera. Using both tube and endpoint agglutination, the antisera reacted and clumped cells of strain 119 at the same frequency as with I-110. This indicates that cell wall antigens in strain 119 are serologically identical to I-110. Antisera prepared against strain 119 also reacted at the same frequency against I-110. A mixture of the antisera did not preferentially agglutinate (clump) any one of the two strains.

9F. Lysis by 110 Phage (virus)

Common 110 phage was obtained from the American Type Culture Collection (Rockville, Md.). The phage was diluted and 1.0 ml portions were spread over a YEM agar plate that had previously been inoculated with 1.0 ml of 10$^6$ I-110 or strain 119 cells. After incubation at 25° C. for 7 days, plaques (consisting of areas of dead cells killed by the phage) were visible and could be counted. The numbers of plaques were identical for both strain 119 and I-110. This indicates that the cell wall receptor sites (phage infections sites) are similar for both strain 119 and I-110.

9G. DNA Restriction Pattern

A variety of common commercial available restriction enzymes including EcoR1, HIND III, Bam H1, Bgl 1, Sal 1, and Xho 1, were used to cut the DNA of strain 119 and I-110 into segments of specific sizes. The DNA was then collected, purified, assayed, and stained. The stains were identical for both strains. This indicates that, whatever genetic differences occur between strain 119 and parental I-110, they were not detectable in DNA restriction patterns. However, small changes in DNA composition may not be detectable within the larger DNA pieces that are obtained with restriction enzyme analysis.

The following Tables 12, 13 and 14 summarize the preceding results of Example 9:

TABLE 12

| HYDROGEN UPTAKE ACTIVITY, AMPEROMETRIC MEASUREMENT (2 REPLICATIONS) | |
|---|---|
| Strain | nmol H$_2$/mg Protein/min. |
| I-110 parental | 10.4 |
| 119 | 11.3 |
| 151 | 16.0 |
| 152 | 8.8 |
| 158 | 12.5 |
| 165 | 12.1 |
| 193 | 9.8 |
| 298 | 19.8 |
| 327 | 8.6 |

TABLE 13

ACETYLENE REDUCTION ACTIVITY, IN VITRO FIXATION (2 REPLICATIONS)

| Strain | nmol $C_2H_4$/mg. Cell mass/hr. |
|---|---|
| I-110 parental | 5.0 |
| 119 | 26.6 |
| 151 | 9.2 |
| 152 | 0.4 |
| 158 | 6.2 |
| 165 | 0.3 |
| 193 | 0.2 |
| 298 | 7.5 |
| 327 | 6.8 |

TABLE 14

COMPARISON OF DISTINGUISHING CHARACTERISTICS OF PARENTAL STRAIN I-110 AND CLONE STRAIN 119

| Characteristic | I-110 Parental | Strain 119 |
|---|---|---|
| Growth in YEM (Example 9A) | Poor | Good |
| Slime Production on RDY (Example 9A) | Normal | Elevated |
| Growth on Succinate (Example 9B) | No | Yes |
| 110 Somatic Agglutination (Example 9E) | Yes | Yes |
| Lysis by 110 Phage (Example 9F) | Yes | Yes |
| DNA Restriction Pattern (Example 9G) | Identical | Identical |
| 21 Kdalton Protein (Example 8) | No | Yes |
| Nodulation (Examples 6 & 7) | Low | High |
| Nitrogenase Activity (Examples 2 and 9D) | Normal | Elevated |
| Competitive Ability (Examples 3, 4 and 5) | Normal | Elevated |
| Kanamycin Resistance | No | Yes |
| (Example 1) Hydrogenase Activity (Example 9C) | Normal | Normal |

Table 14 summarizes the important biochemical differences between strain 119 and its I-110 parental strain. Strain 119 is particularly characterized by its growth in YEM and succinate media, and its enhanced nodulation and competitiveness properties. The foregoing profile of properties distinguishes strain 119 from other known strains of *Bradyrhizobium japonicum*.

It ill be understood that the above description is of perferred exemplary embodiments of the invention, and that the invention is not limited to the specific form shown, particularly the specific strain 119. Strain 119 is the most superior member of a class of mutant clones provided by the present invention and characterized by the properties listed in the preceding Table 14. The genetic matter of strain 119 comprises a genome having genetic means defining such characteristics. The invention in its broad aspect embraces any *Bradyrhizobium japonicum* mutant having the characteristics summarized in Table 14. Thus, it will be understood that the term *Bradyrhizobium japonicum* strain 119 as used herein embraces not only the aforementioned deposited strains, but also mutants derived therefrom and other *Bradyrhizobium japonicum* strains having the essential genetic characteristics thereof.

We claim:

1. A *Bradyrhizobium japonicum* strain 119 having deposit number NRRL-B-15822 or NRRL-B-15823.

2. An inoculum suitable for inoculation of soybean to enhance nodulation thereof, comprising the strain of claim 1 in combination with a particulate carrier.

3. The inoculum of claim 2, wherein said carrier is peat.

* * * * *